United States Patent
Bittner et al.

(10) Patent No.: US 9,751,905 B2
(45) Date of Patent: *Sep. 5, 2017

(54) PROCESS FOR EXTRACTING MINERAL OIL USING SURFACTANTS BASED ON BUTYLENE OXIDE-CONTAINING ALKYL ALKOXYLATES

(71) Applicant: BASF SE, Ludwigshafen (DE)

(72) Inventors: Christian Bittner, Bensheim (DE); Günter Oetter, Frankenthal (DE); Jack Tinsley, Houston, TX (US); Christian Spindler, Houston, TX (US); Gabriela Alvarez-Juergenson, Mannheim (DE); Sophie Vogel, Mannheim (DE)

(73) Assignee: BASF SE, Ludwigshafen (DE)

( * ) Notice: Subject to any disclaimer, the term of this patent is extended or adjusted under 35 U.S.C. 154(b) by 203 days.

This patent is subject to a terminal disclaimer.

(21) Appl. No.: 14/081,027

(22) Filed: Nov. 15, 2013

(65) Prior Publication Data
US 2014/0155645 A1 Jun. 5, 2014

Related U.S. Application Data

(63) Continuation of application No. 13/044,345, filed on Mar. 9, 2011, now Pat. No. 8,607,865.

(60) Provisional application No. 61/312,292, filed on Mar. 10, 2010.

(51) Int. Cl.
| | |
|---|---|
| C09K 8/584 | (2006.01) |
| C07F 9/46 | (2006.01) |
| B01F 17/00 | (2006.01) |
| C07C 305/06 | (2006.01) |

(52) U.S. Cl.
CPC ............ *C07F 9/46* (2013.01); *B01F 17/0021* (2013.01); *C07C 305/06* (2013.01); *C09K 8/584* (2013.01)

(58) Field of Classification Search
CPC .......... C09K 8/528; C09K 8/524; C09K 8/72; C09K 8/80; C09K 8/805; C09K 17/28; C09K 17/40; C09K 2208/12; C09K 3/00; C09K 8/035; C09K 8/08; C09K 8/38; C09K 8/467; C09K 8/487; C09K 8/508; C09K 8/50; C09K 8/5086; C09K 8/54; C09K 8/5751; C09K 8/5755; C09K 8/5756; C09K 8/604; C09K 8/92; C09K 3/10; C09K 5/10; C09K 8/12; C09K 8/22; C09K 8/536; C09K 8/594; C09K 8/62; C09K 8/68; C09K 8/88; C09K 8/94; C09K 8/584; E21B 43/16; E21B 43/162; E21B 43/20; E21B 43/267; E21B 21/14; E21B 33/13; E21B 37/06; E21B 43/166; E21B 7/00
See application file for complete search history.

(56) References Cited

U.S. PATENT DOCUMENTS

| | | | |
|---|---|---|---|
| 3,843,706 A * | 10/1974 | Weil | C11D 1/29 510/495 |
| 3,890,239 A | 6/1975 | Dycus et al. | |
| 4,259,215 A * | 3/1981 | Murata | C11D 1/29 510/329 |
| 4,293,428 A | 10/1981 | Gale et al. | |
| 4,393,935 A | 7/1983 | Walton | |
| 4,395,364 A | 7/1983 | Murata et al. | |
| 4,448,697 A | 5/1984 | McCoy et al. | |
| 4,460,481 A | 7/1984 | Schievelbein | |
| 4,592,875 A * | 6/1986 | Kesling, Jr. | C07C 305/00 510/537 |
| 4,608,197 A * | 8/1986 | Kesling, Jr. | C07C 305/00 510/537 |
| 4,722,396 A | 2/1988 | Balzer | |
| 4,983,323 A | 1/1991 | Cox et al. | |
| 5,110,487 A | 5/1992 | Current | |
| 5,741,947 A | 4/1998 | Wolf et al. | |
| 7,985,718 B2 | 7/2011 | Steinbrenner et al. | |
| 8,034,757 B2 | 10/2011 | Murata et al. | |
| 8,080,588 B2 | 12/2011 | Bittner et al. | |
| 8,124,658 B2 | 2/2012 | Bittner et al. | |
| 8,461,219 B2 | 6/2013 | Steiner et al. | |
| 8,475,662 B2 | 7/2013 | Domke et al. | |

(Continued)

FOREIGN PATENT DOCUMENTS

| | | |
|---|---|---|
| DE | 4325237 A1 | 2/1995 |
| DE | 10243361 A1 | 4/2004 |

(Continued)

OTHER PUBLICATIONS

S.S. Talmage, Environmental and Human safety of major surfactant, 1994, p. 12.*
U.S. Appl. No. 61/260,031.
U.S. Appl. No. 61/312,299.
U.S. Appl. No. 61/315,051.
U.S. Appl. No. 61/325,051.
G. Casiraghi, G. Casnati and M. Cornia, Tetrahedron Letters, No. 9, 679-682 (1973).
M. B. Dinger and M. J. Scott describe in Chem. Commun., 1999. 2525/2526.
M. B. Dinger and M. J. Scott, Inorg. Chem. 2000, 39, 1238-1254.
M. B. Dinger and M. J. Scott , Inorg. Chem. 2001 40, 1029-1036.
M. B. Dinger and M. J. Scott, Eur J. Org. Chem. 2000, 2467-2478.
K. Matloka, A. Gelis, M. Regalbuto, G. Vandegift and M. J. Scott, Dalton Trans., 2005, 3719-3721.

(Continued)

*Primary Examiner* — Kumar R Bhushan
(74) *Attorney, Agent, or Firm* — Drinker Biddle & Reath LLP

(57) ABSTRACT

A surfactant and a surfactant formulation comprising at least one ionic surfactant of the general formula $R^1$—O-$(D)_n$-$(B)_m$-$(A)_l$-$XY^-M^+$ where $R^1$ is a linear or branched, saturated or unsaturated, aliphatic and/or aromatic hydrocarbon radical having 8 to 30 carbon atoms, A is ethyleneoxy, B is propyleneoxy, and D is butyleneoxy, l is from 0 to 99, m is from 0 to 99 and n is from 1 to 99, X is an alkyl or alkylene group having 0 to 10 carbon atoms, $M^+$ is a cation, and $Y^-$ is selected from the group of sulfate groups, sulfonate groups, carboxylate groups and phosphate groups.

11 Claims, No Drawings

(56) References Cited

U.S. PATENT DOCUMENTS

| | | |
|---|---|---|
| 2008/0194435 A1 | 8/2008 | Huff et al. |
| 2009/0131260 A1* | 5/2009 | Kober .................. A01N 25/10 504/367 |
| 2009/0264598 A1* | 10/2009 | Bittner ................ B01F 17/0021 525/231 |
| 2009/0270281 A1 | 10/2009 | Steinbrenner et al. |
| 2011/0083846 A1 | 4/2011 | Bittner et al. |
| 2011/0083847 A1 | 4/2011 | Bittner et al. |
| 2011/0083848 A1 | 4/2011 | Bittner et al. |
| 2011/0201497 A1 | 8/2011 | Klingelhoefer et al. |
| 2011/0220353 A1 | 9/2011 | Bittner et al. |
| 2011/0220364 A1 | 9/2011 | Bittner et al. |
| 2011/0220365 A1 | 9/2011 | Bittner et al. |
| 2011/0220366 A1 | 9/2011 | Bittner et al. |
| 2011/0259583 A1 | 10/2011 | Bittner et al. |
| 2011/0263467 A1 | 10/2011 | Bittner et al. |
| 2011/0281779 A1 | 11/2011 | Weerasooriya et al. |
| 2011/0288322 A1 | 11/2011 | Garcia et al. |

FOREIGN PATENT DOCUMENTS

| | | |
|---|---|---|
| EP | 0392667 A2 | 10/1990 |
| WO | WO-2006/131541 A1 | 12/2006 |
| WO | WO-2008/090267 A2 | 7/2008 |
| WO | WO-2009/084729 A1 | 7/2009 |

OTHER PUBLICATIONS

K. Matloka, A. Gelis, M. Regalbuto, G. Vandegift and M. J. Scott, Separation Science and Technology, 41: 2006, 2129-2146.

M. W. Peters, E. J. Werner and M. J. Scott, Inorg. Chem., 2002, 41, 1701-1716.

R. Mitra, M.W. Peters and M. Scott, Dalton Trans., 2007, 3924-3935.

H. Hoffmann et al., Adv. Colloid Interface Sd. 1982, 17, 275-298.

M. R. Rojas et al., Journal of Colloid and Interface Science 342 (2010) 103-109.

Versteeg et al. Chemosphere 24(1992) 641-662.

* cited by examiner

PROCESS FOR EXTRACTING MINERAL OIL USING SURFACTANTS BASED ON BUTYLENE OXIDE-CONTAINING ALKYL ALKOXYLATES

CROSS-REFERENCE TO RELATED APPLICATIONS

This application is a continuation application of U.S. patent application Ser. No. 13/044,345, filed Mar. 9, 2011, which claims benefit of U.S. Provisional Patent Application Ser. No. 61/312,292, filed Mar. 10, 2010, the contents of each of which are incorporated herein by reference.

BACKGROUND OF THE INVENTION

The invention relates to a process for mineral oil extraction by means of Winsor Type III microemulsion flooding, in which an aqueous surfactant formulation comprising at least one ionic surfactant of the general formula

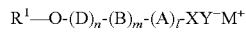

is injected through injection boreholes into a mineral oil deposit, and crude oil is withdrawn from the deposit through production boreholes. The invention further relates to ionic surfactants of the general formula, and to processes for preparation thereof.

In natural mineral oil deposits, mineral oil is present in the cavities of porous reservoir rocks which are sealed toward the surface of the earth by impervious top layers. The cavities may be very fine cavities, capillaries, pores or the like. Fine pore necks may, for example, have a diameter of only about 1 μm. As well as mineral oil, including fractions of natural gas, a deposit comprises water with a greater or lesser salt content.

In mineral oil extraction, a distinction is generally drawn between primary, secondary and tertiary extraction. In primary extraction, the mineral oil flows, after commencement of drilling of the deposit, of its own accord through the borehole to the surface owing to the autogenous pressure of the deposit.

After primary extraction, secondary extraction is therefore used. In secondary extraction, in addition to the boreholes which serve for the extraction of the mineral oil, the so-called production bores, further boreholes are drilled into the mineral oil-bearing formation. Water is injected into the deposit through these so-called injection bores in order to maintain the pressure or to increase it again. As a result of the injection of the water, the mineral oil is forced slowly through the cavities into the formation, proceeding from the injection bore in the direction of the production bore. However, this only works for as long as the cavities are completely filled with oil and the more viscous oil is pushed onward by the water. As soon as the mobile water breaks through cavities, it flows on the path of least resistance from this time, i.e. through the channel formed, and no longer pushes the oil onward.

By means of primary and secondary extraction, generally only approx. 30 to 35% of the amount of mineral oil present in the deposit can be extracted.

It is known that the mineral oil yield can be enhanced further by measures for tertiary oil extraction. A review of tertiary oil extraction can be found, for example, in "Journal of Petroleum Science of Engineering 19 (1998)", pages 265 to 280. Tertiary oil extraction includes, for example, thermal methods in which hot water or steam is injected into the deposit. This lowers the viscosity of the oil. The flow medium used may likewise be gases such as $CO_2$ or nitrogen.

Tertiary mineral oil extraction also includes methods in which suitable chemicals are used as assistants for oil extraction. These can be used to influence the situation toward the end of the water flow and as a result also to extract mineral oil hitherto held firmly within the rock formation.

Viscous and capillary forces act on the mineral oil which is trapped in the pores of the deposit rock toward the end of the secondary extraction, the ratio of these two forces relative to one another being determined by the microscopic oil separation. By means of a dimensionless parameter, the so-called capillary number, the action of these forces is described. It is the ratio of the viscosity forces (velocity x viscosity of the forcing phase) to the capillary forces (interfacial tension between oil and water x wetting of the rock):

$$n_c = \frac{\mu v}{\sigma \cos \theta}.$$

In this formula, μ is the viscosity of the fluid mobilizing mineral oil, ν is the Darcy velocity (flow per unit area), σ is the interfacial tension between liquid mobilizing mineral oil and mineral oil, and θ is the contact angle between mineral oil and the rock (C. Melrose, C. F. Brandner, J. Canadian Petr. Techn. 58, October-December, 1974). The higher the capillary number, the greater the mobilization of the oil and hence also the degree of oil removal.

It is known that the capillary number toward the end of secondary mineral oil extraction is in the region of about $10^{-6}$ and that it is necessary to increase the capillary number to about $10^{-3}$ to $10^{-2}$ in order to be able to mobilize additional mineral oil.

For this purpose, it is possible to conduct a particular form of the flooding method—what is known as Winsor type III microemulsion flooding. In Winsor type III microemulsion flooding, the injected surfactants should form a Winsor type III microemulsion with the water phase and oil phase present in the deposit. A Winsor type III microemulsion is not an emulsion with particularly small droplets, but rather a thermodynamically stable, liquid mixture of water, oil and surfactants. The three advantages thereof are that

- a very low interfacial tension a between mineral oil and aqueous phase is thus achieved,
- it generally has a very low viscosity and as a result is not trapped in a porous matrix,
- it forms with even the smallest energy inputs and can remain stable over an infinitely long period (conventional emulsions, in contrast, require high shear forces which predominantly do not occur in the reservoir, and are merely kinetically stabilized).

The Winsor type III microemulsion is in an equilibrium with excess water and excess oil. Under these conditions of microemulsion formation, the surfactants cover the oil-water interface and lower the interfacial tension a more preferably to values of $<10^{-2}$ mN/m (ultra-low interfacial tension). In order to achieve an optimal result, the proportion of the microemulsion in the water-microemulsion-oil system, with a defined amount of surfactant, should by its nature be at a maximum, since this allows lower interfacial tensions to be achieved.

In this manner, it is possible to alter the form of the oil droplets (interfacial tension between oil and water is lowered to such a degree that the smallest interface state is no longer favored and the spherical form is no longer preferred), and they can be forced through the capillary openings by the flooding water.

When all oil-water interfaces are covered with surfactant, in the presence of an excess amount of surfactant, the Winsor type III microemulsion forms. It thus constitutes a reservoir for surfactants which cause a very low interfacial tension between oil phase and water phase. By virtue of the Winsor type III microemulsion being of low viscosity, it also migrates through the porous deposit rock in the flooding process (emulsions, in contrast, can become trapped in the porous matrix and block deposits). When the Winsor type III microemulsion meets an oil-water interface as yet uncovered with surfactant, the surfactant from the microemulsion can significantly lower the interfacial tension of this new interface, and lead to mobilization of the oil (for example by deformation of the oil droplets).

The oil droplets can subsequently combine to a continuous oil bank. This has two advantages:

Firstly, as the continuous oil bank advances through new porous rock, the oil droplets present there can coalesce with the bank.

Moreover, the combination of the oil droplets to give an oil bank significantly reduces the oil-water interface and hence surfactant no longer required is released again. Thereafter, the surfactant released, as described above, can mobilize oil droplets remaining in the formation.

Winsor type III microemulsion flooding is consequently an exceptionally efficient process, and requires much less surfactant compared to an emulsion flooding process. In microemulsion flooding, the surfactants are typically optionally injected together with co-solvents and/or basic salts (optionally in the presence of chelating agents). Subsequently, a solution of thickened polymer is injected for mobility control. A further variant is the injection of a mixture of thickening polymer and surfactants, co-solvents and/or basic salts (optionally with chelating agent), and then a solution of thickening polymer for mobility control. These solutions should generally be clear in order to prevent blockages of the reservoir.

The requirements on surfactants for tertiary mineral oil extraction differ significantly from requirements on surfactants for other applications: suitable surfactants for tertiary oil extraction should reduce the interfacial tension between water and oil (typically approx. 20 mN/m) to particularly low values of less than $10^{-2}$ mN/m in order to enable sufficient mobilization of the mineral oil. This has to be done at the customary deposit temperatures of approx. 15° C. to 130° C. and in the presence of water of high salt contents, more particularly also in the presence of high proportions of calcium and/or magnesium ions; the surfactants thus also have to be soluble in deposit water with a high salt content.

To fulfill these requirements, there have already been frequent proposals of mixtures of surfactants, especially mixtures of anionic and nonionic surfactants.

U.S. Pat. No. 3,890,239 discloses a combination of organic sulfonates with alkyl alkoxylates of the $C_8$-$C_{20}$-AO—H type (AO=alkylene oxide having 2 to 6 carbon atoms) with anionic surfactants of the $C_8$-$C_{20}$-AO-sulfate or $C_8$-$C_{20}$-AO-sulfonate type. The specification of the alkylene oxides is only kept very general in the context of the disclosure of U.S. Pat. No. 3,890,239. However, there are only examples which comprise exclusively EO.

U.S. Pat. No. 4,448,697 claims the use of alkyl alkoxylates of the $C_1$-$C_6$-$(AO)_{1-40}$-$EO_{\geq 10}$—H type in combination with an anionic surfactant. AO may be 1,2-butylene oxide or 2,3-butylene oxide.

U.S. Pat. No. 4,460,481 describes surfactants of the alkylaryl alkoxy sulfate or sulfonate type. The alkylene oxide may be ethylene oxide, propylene oxide or butylene oxide. There exists the proviso that ethylene oxide makes up the majority of the alkylene oxides. There is no more detailed description of the butylene oxide.

The use parameters, for example type, concentration and mixing ratio of the surfactants used with respect to one another, are therefore adjusted by the person skilled in the art according to the conditions existing in a given oil formation (for example temperature and salt content).

As described above, mineral oil production is proportional to the capillary number. The lower the interfacial tension between oil and water, the higher it is. The higher the mean number of carbon atoms in the crude oil, the more difficult it is to achieve low interfacial tension. Suitable surfactants for low interfacial tensions are those which possess a long alkyl radical. The longer the alkyl radical, the better it is possible to reduce the interfacial tensions. However, the availability of such compounds is very limited.

It is therefore an object of the invention to provide a particularly efficient surfactant for use for surfactant flooding, and an improved process for tertiary mineral oil extraction.

BRIEF SUMMARY OF THE INVENTION

Accordingly, a process is provided for tertiary mineral oil extraction by means of Winsor type III microemulsion flooding, in which an aqueous surfactant formulation comprising at least one ionic surfactant is injected through at least one injection borehole into a mineral oil deposit, the interfacial tension between oil and water is lowered to values of <0.1 mN/m, preferably to values of <0.05 mN/m, more preferably to values of <0.01 mN/m, and crude oil is withdrawn from the deposit through at least one production borehole, wherein the surfactant formulation comprises at least one surfactant of the general formula

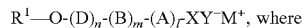, where $R^1$ is a linear or branched, saturated or unsaturated, aliphatic and/or aromatic hydrocarbon radical having 8 to 30 carbon atoms,
A is ethyleneoxy,
B is propyleneoxy, and
D is butyleneoxy,
l is from 0 to 99,
m is from 0 to 99 and
n is from 1 to 99,
X is an alkyl or alkylene group having 0 to 10 carbon atoms,
$M^+$ is a cation, and
$Y^-$ is selected from the group of sulfate groups, sulfonate groups, carboxylate groups and phosphate groups, where
the A, B and D groups may be distributed randomly, alternatingly, or in the form of two, three, four or more blocks in any sequence, the sum of l+m+n is in the range from 3 to 99 and the proportion of 1,2-butylene oxide, based on the total amount of butylene oxide, is at least 80%.

Additionally provided has been a surfactant mixture for mineral oil extraction, which comprises at least one ionic surfactant of the general formula defined above.

DETAILED DESCRIPTION OF THE INVENTION

With regard to the invention, the following should be stated specifically:

In the above-described process according to the invention for mineral oil extraction by means of Winsor type III microemulsion flooding, an aqueous surfactant formulation comprising at least one surfactant of the general formula is used. It may additionally comprise further surfactants and/or other components.

In the process according to the invention for tertiary mineral oil extraction by means of Winsor type III microemulsion flooding, the use of the inventive surfactant lowers the interfacial tension between oil and water to values of <0.1 mN/m, preferably to <0.05 mN/m, more preferably to <0.01 mN/m. The interfacial tension between oil and water is thus lowered to values in the range from 0.1 mN/m to 0.0001 mN/m, preferably to values in the range from 0.05 mN/m to 0.0001 mN/m, more preferably to values in the range from 0.01 mN/m to 0.0001 mN/m.

The at least one surfactant can be encompassed by the general formula $R^1$—O-(D)$_n$-(B)$_m$-(A)$_l$-XY$^-$M$^+$. As a result of the preparation, it is also possible for a plurality of different surfactants of the general formula to be present in the surfactant formulation.

The $R^1$ radical is a straight-chain or branched aliphatic and/or aromatic hydrocarbon radical having 8 to 30 carbon atoms, preferably 9 to 30 carbon atoms, more preferably 10 to 28 carbon atoms.

In a particularly preferred embodiment of the invention, the $R^1$ radical is iso-$C_{17}H_{35}$ or a commercial fatty alcohol mixture consisting of linear $C_{16}H_{33}$ and $C_{18}H_{37}$ or derived from the commercially available $C_{16}$ Guerbet alcohol 2-hexyldecan-1-ol or derived from the commercially available $C_{24}$ Guerbet alcohol 2-decyltetradecanol or derived from the commercially available $C_{28}$ Guerbet alcohol 2-dodecylhexadecanol.

More preferably, in linear alcohols n=3 to 10 and m=5 to 9, while, in branched alcohols n=2 to 10 and m=5 to 9. It is preferred here in each case that D is 1,2-butylene oxide to an extent of more than 80%, and that the alkylene oxides, beginning at the alcohol, have the sequence D-B-A. The alkylene oxides are arranged in blocks to an extent of more than 90%.

Particular preference is given to a straight-chain or branched aliphatic hydrocarbon radical, especially a straight-chain or branched aliphatic hydrocarbon radical having 10 to 28 carbon atoms.

A branched aliphatic hydrocarbon radical generally has a degree of branching of 0.1 to 5.5, preferably 1 to 3.5. The term "degree of branching" is defined here in a manner known in principle as the number of methyl groups in a molecule of the alcohol minus 1. The mean degree of branching is the statistical mean of the degrees of branching of all molecules in a sample.

In the above formula, A means ethyleneoxy. B means propyleneoxy and D means butyleneoxy.

In the above-defined general formula l, m and n are each integers. It is, however, clear to the person skilled in the art in the field of polyalkoxylates that this definition is the definition of a single surfactant in each case. In the case of presence of surfactant mixtures or surfactant formulations which comprise a plurality of surfactants of the general formula, the numbers l, m and n are each mean values over all molecules of the surfactants, since the alkoxylation of alcohol with ethylene oxide and/or propylene oxide and/or butylene oxide in each case affords a certain distribution of chain lengths. This distribution can be described in a manner known in principle by the polydispersity D. $D=M_w/M_n$ is the quotient of the weight-average molar mass and the number-average molar mass. The polydispersity can be determined by means of the methods known to those skilled in the art, for example by means of gel permeation chromatography.

In the above general formula l is from 0 to 99, preferably 1 to 40, more preferably 1 to 20.

In the above general formula m is from 0 to 99, preferably 1 to 20, more preferably 5 to 9.

In the above general formula n is from 1 to 99, preferably 2 to 30, more preferably 2 to 10.

According to the invention, the sum of l+m+n is a number in the range from 3 to 99, preferably in the range from 5 to 50, more preferably in the range from 8 to 39.

According to the present invention the proportion of 1,2-butyleneoxy, based on the total amount of butyleneoxy (D), is at least 80%, preferably at least 85%, preferably at least 90%, more preferably at least 95%, of 1,2-butyleneoxy.

The ethyleneoxy (A), propyleneoxy (B) and butyleneoxy (D) group(s) are randomly distributed, alternatingly distributed, or are in the form of two, three, four, five or more blocks in any sequence.

In a preferred embodiment of the invention, in the presence of a plurality of different alkyleneoxy blocks, the sequence R1, butyleneoxy block, propyleneoxy block, ethyleneoxy block is preferred. The butylene oxide used should comprise ≥80% of 1,2-butylene oxide, preferably >90% of 1,2-butylene oxide.

In the above general formula, X is an alkylene group or alkenylene group having 0 to 10, preferably 0 to 3 carbon atoms. The alkylene group is preferably a methylene, ethylene or propylene group.

In the prior art cited, there is often no specific information with regard to the description of $C_4$ epoxides. This may generally be understood to mean 1,2-butylene oxide, 2,3-butylene oxide, isobutylene oxide, and mixtures of these compounds. The composition is generally dependent on the $C_4$ olefin used, and to a certain degree on the oxidation process.

In the above general formula Y is a sulfonate, sulfate or carboxyl group or phosphate group.

In the above formula $M^+$ is a cation, preferably a cation selected from the group of $Na^+$, $K^+$, $Li^+$, $NH_4^+$, $H^+$, $Mg^{2+}$ and $Ca^{2+}$.

The surfactants of the general formula can be prepared in a manner known in principle by alkoxylating corresponding alcohols $R^1$—OH. The performance of such alkoxylation is known in principle to those skilled in the art. It is likewise known to those skilled in the art that the molar mass distribution of the alkoxylates can be influenced through the reaction conditions, especially the selection of the catalyst.

The surfactants of the general formula can preferably be prepared by base-catalyzed alkoxylation. In this case, the alcohol $R^1$—OH can be admixed in a pressure reactor with alkali metal hydroxides, preferably potassium hydroxide, or with alkali metal alkoxides, for example sodium methoxide. Water still present in the mixture can be drawn off by means of reduced pressure (for example <100 mbar) and/or increasing the temperature (30 to 150° C.). Thereafter, the alcohol is present in the form of the corresponding alkoxide. This is followed by intertization with inert gas (for example nitrogen) and stepwise addition of the alkylene oxide(s) at temperatures of 60 to 180° C. up to a maximum pressure of 10 bar. In a preferred embodiment, the alkylene oxide is metered in initially at 130° C. In the course of the reaction, the temperature rises up to 170° C. as a result of the heat of reaction released. In a further preferred embodiment of the invention, the butylene oxide is first added at a temperature in the range from 135 to 145° C., then the propylene oxide is added at a temperature in the range from 130 to 145° C., and then the ethylene oxide is added at a temperature in the range from 125 to 145° C. At the end of the reaction, the catalyst can be centralized, for example, by adding acid (for example acetic acid or phosphoric acid) and filtered off if required.

However, the alkoxylation of the alcohols $R^1$—OH can also be undertaken by means of other methods, for example by acid-catalyzed alkoxylation. In addition, it is possible to use, for example double hydroxide clays, as described in DE 4325237 A1, or it is possible to use double metal cyanide catalysts (DMC catalysts). Suitable DMC catalysts are disclosed, for example in DE 10243361 A1, especially in paragraphs [0029] to [0041] and the literature cited therein. For example, it is possible to use catalysts of the Zn—Co type. To perform the reaction, the alcohol $R^1$—OH can be admixed with the catalyst, and the mixture can be dewatered as described above and reacted with the alkylene oxides as described. Typically not more than 1000 ppm of catalyst based on the mixture are used, and the catalyst can remain in the product owing to this small amount. The amount of catalyst may generally be less than 1000 ppm, for example 250 ppm or less.

The anionic group is finally introduced. This is known in principle to those skilled in the art. In the case of a sulfate group, it is possible, for example, to employ the reaction with sulfuric acid, chlorosulfonic acid or sulfur trioxide in a falling-film reactor with subsequent neutralization. In the case of a sulfonate group it is possible, for example, to employ the reaction with propane sultone and subsequent neutralization, with butane sultone and subsequent neutralization, with vinylsulfonic acid sodium salt, or with 3-chloro-2-hydroxypropanesulfonic acid sodium salt. In the case of a carboxylate group, it is possible, for example, to employ the oxidation of the alcohol with oxygen and subsequent neutralization, or the reaction with chloroacetic acid sodium salt.

Further Surfactants

In addition to the surfactants of the general formula, the formulation may additionally optionally comprise further surfactants. These are, for example, anionic surfactants of the alkylarylsulfonate or olefinsulfonate (alpha-olefinsulfonate or internal olefinsulfonate) type and/or nonionic surfactants of the alkyl ethoxylate or alkyl polyglucoside type. These further surfactants may especially also be oligomeric or polymeric surfactants. It is advantageous to use such polymeric co-surfactants to reduce the amount of surfactants needed to form a microemulsion. Such polymeric co-surfactants are therefore also referred to as "microemulsion boosters". Examples of such polymeric surfactants comprise amphiphilic block copolymers which comprise at least one hydrophilic block and at least one hydrophobic block. Examples comprise polypropylene oxide-polyethylene oxide block copolymers, polyisobutene-polyethylene oxide block copolymers, and comb polymers with polyethylene oxide side chains and a hydrophobic main chain, where the main chain preferably comprises essentially olefins or (meth)acrylates as monomers. The term "polyethylene oxide" here should in each case include polyethylene oxide blocks comprising propylene oxide units as defined above. Further details of such surfactants are disclosed in WO 2006/131541 A1.

Process for Mineral Oil Extraction

In the process according to the invention for mineral oil extraction, a suitable aqueous formulation of the surfactants of the general formula is injected through at least one injection borehole into the mineral oil deposit, and crude oil is withdrawn from the deposit through at least one production borehole. The term "crude oil" in this context of course does not mean single-phase oil, but rather the usual crude oil-water emulsions. In general, a deposit is provided with several injection boreholes and with several production boreholes.

The main effect of the surfactant lies in the reduction of the interfacial tension between water and oil—desirably to values significantly <0.1 mN/m. After the injection of the surfactant formulation, known as "surfactant flooding", or preferably the Winsor type III "microemulsion flooding", the pressure can be maintained by injecting water into the formation ("water flooding") or preferably a higher-viscosity aqueous solution of a polymer with strong thickening action ("polymer flooding"). Also known, however, are techniques by which the surfactants are first of all allowed to act on the formation. A further known technique is the injection of a solution of surfactants and thickening polymers, followed by a solution of thickening polymer. The person skilled in the art is aware of details of the industrial performance of "surfactant flooding", "water flooding", and "polymer flooding", and employs an appropriate technique according to the type of deposit.

For the process according to the invention, an aqueous formulation which comprises surfactants of the general formula is used. In addition to water, the formulations may optionally also comprise water-miscible or at least water-dispersible organic substances or other substances. Such additives serve especially to stabilize the surfactant solution during storage or transport to the oil field. The amount of such additional solvents should, however, generally not exceed 50% by weight, preferably 20% by weight. In a particularly advantageous embodiment of the invention, exclusively water is used for formulation. Examples of water-miscible solvents include especially alcohols such as methanol, ethanol and propanol, butanol, sec-butanol, pentanol, butyl ethylene glycol, butyl diethylene glycol or butyl triethylene glycol.

According to the invention, the proportion of the surfactants of the general formula is at least 30% by weight based on the proportion of all surfactants present, i.e. the surfactants of the general formula and optionally present surfactants. The proportion is preferably at least 50% by weight.

The mixture used in accordance with the invention can preferably be used for surfactant flooding of deposits. It is especially suitable for Winsor type III microemulsion flooding (flooding in the Winsor III range or in the range of existence of the bicontinuous microemulsion phase). The technique of microemulsion flooding has already been described in detail at the outset.

In addition to the surfactants, the formulations may also comprise further components, for example $C_4$- to $C_8$ alcohols and/or basic salts (so-called "alkali surfactant flooding"). Such additives can be used, for example, to reduce retention in the formation. The ratio of the alcohols based on the total amount of surfactant used is generally at least 1:1—however, it is also possible to use a significant excess of alcohol. The amount of basic salts may typically range from 0.1% by weight to 5% by weight.

The deposits in which the process is employed generally have a temperature of at least 10° C., for example 10 to 150° C., preferably a temperature of at least 15° C. to 120° C. The total concentration of all surfactants together is 0.05 to 5% by weight, based on the total amount of the aqueous surfactant formulation, preferably 0.1 to 2.5% by weight. The person skilled in the art makes a suitable selection according to the desired properties, especially according to the conditions in the mineral oil formation. It is clear here to the person skilled in the art that the concentration of the surfactants can change after injection into the formation because the formulation can mix with formation water, or surfactants can also be absorbed on solid surfaces of the formation. It is the great advantage of the mixture used in accordance with the invention that the surfactants lead to a particularly good lowering of interfacial tension.

It is of course possible and also advisable first to prepare a concentrate which is only diluted on site to the desired concentration for injection into the formation. In general, the total concentration of the surfactants in such a concentrate is 10 to 45% by weight.

The examples which follow are intended to illustrate the invention in detail:

Part I: Synthesis of the Surfactants
General Method 1: Alkoxylation by Means of KOH Catalysis (Applies to Use of EO, PO and/or 1,2-BuO)

In a 2 l autoclave, the alcohol to be alkoxylated (1.0 eq) is admixed with an aqueous KOH solution which comprises 50% by weight of KOH. The amount of KOH is 0.2% by weight of the product to be prepared. While stirring, the mixture is dewatered at 100° C. and 20 mbar for 2 h. This is followed by purging three times with $N_2$, establishment of a feed pressure of approx. 1.3 bar of $N_2$ and a temperature increase to 120 to 130° C. The alkylene oxide is metered in such that the temperature remains between 125° C. and 135° C. (in the case of ethylene oxide) or 130 and 140° C. (in the case of propylene oxide) or 135 and 145° C. (in the case of 1,2-butylene oxide). This is followed by stirring at 125 to 145° C. for a further 5 h, purging with $N_2$, cooling to 70° C. and emptying of the reactor. The basic crude product is neutralized with the aid of acetic acid. Alternatively, the neutralization can also be effected with commercial magnesium silicates, which are subsequently filtered off. The light-colored product is characterized with the aid of a $^1H$ NMR spectrum in $CDCl_3$, gel permeation chromatography and OH number determination, and the yield is determined.

General Method 2: Alkoxylation by Means of DMC Catalysis in the Case of 2,3-butylene oxide In a 2 l autoclave, the alcohol to be alkoxylated (1.0 eq) is mixed with a double metal cyanide catalyst (for example DMC catalyst of the Zn—Co type from BASF) at 80° C. To activate the catalyst, approximately 20 mbar is applied at 80° C. for 1 h. The amount of DMC is 0.1% by weight or less of the product to be prepared. This is followed by purging three times with $N_2$, establishment of a feed pressure of approx. 1.3 bar of $N_2$ and a temperature increase to 120 to 130° C. The alkylene oxide is metered in such that the temperature remains between 125° C. and 135° C. (in the case of ethylene oxide) or 130 and 140° C. (in the case of propylene oxide) or 135 and 145° C. (in the case of 2,3-butylene oxide). This is followed by stirring at 125 to 145° C. for a further 5 h, purging with $N_2$, cooling to 70° C. and emptying of the reactor. The light-colored product is characterized with the aid of a $^1H$ NMR spectrum in $CDCl_3$, gel permeation chromatography and OH number determination, and the yield is determined.

General Method 3: Sulfation by Means of Chlorosulfonic Acid

In a 1 l round-bottom flask, the alkyl alkoxylate to be sulfated (1.0 eq) is dissolved in 1.5-times the amount of dichloromethane (based on percent by weight) and cooled to 5 to 10° C. Thereafter, chlorosulfonic acid (1.1 eq) is added dropwise such that the temperature does not exceed 10° C. The mixture is allowed to warm up to room temperature and is stirred under an $N_2$ stream at this temperature for 4 h before the above reaction mixture is added dropwise to an aqueous NaOH solution of half the volume at max. 15° C. The amount of NaOH is calculated to give rise to a slight excess based on the chlorosulfonic acid used. The resulting pH is approx. pH 9 to 10. The dichloromethane is removed at max. 50° C. on a rotary evaporator under gentle vacuum.

The product is characterized by $^1H$ NMR and the water content of the solution is determined (approx. 70%).

For the synthesis, the following alcohols were used.

| Alcohol | Description |
|---|---|
| $iC_{17}$ | iso-$C_{17}H_{35}$—OH; oxo alcohol, prepared by hydroformylating isohexadecene, which is obtained by tetramerizing butene. The mean degree of branching of the alcohol is 3.1. |
| $C_{16}C_{18}$ | Commercially available fatty alcohol mixture consisting of linear $C_{16}H_{33}$—OH and $C_{18}H_{37}$—OH |
| $C_{16}$ | Commercially available $C_{16}$ Guerbet alcohol |
| Guerbet | (2-hexyldecan-1-ol) |

Performance Tests

The surfactants obtained were used to carry out the following tests in order to assess the suitability thereof for tertiary mineral oil extraction.

Description of the Test Methods
Determination of SP*
a) Principle of the Measurement:

The interfacial tension between water and oil was determined in a known manner via the measurement of the solubilization parameter SP*. The determination of the interfacial tension via the determination of the solubilization parameter SP* is a method for approximate determination of the interfacial tension which is accepted in the technical field. The solubilization parameter SP* indicates how many ml of oil are dissolved per ml of surfactant used in a microemulsion (Winsor type III). The interfacial tension σ (IFT) can be calculated therefrom via the approximate formula $IFT \approx 0.3/(SP^*)^2$, if equal volumes of water and oil are used (C. Huh, J. Coll. Interf. Sc., Vol. 71, No. 2 (1979)).

b) Procedure

To determine the SP*, a 100 ml measuring cylinder with a magnetic stirrer bar is filled with 20 ml of oil and 20 ml of water. To this are added the concentrations of the particular surfactants. Subsequently, the temperature is increased stepwise from 20 to 90° C., and the temperature window in which a microemulsion forms is observed.

The formation of the microemulsion can be assessed visually or else with the aid of conductivity measurements. A triphasic system forms (upper oil phase, middle microemulsion phase, lower water phase). When the upper and lower phase are of equal size and do not change over a period of 12 h, the optimal temperature ($T_{opt}$) of the microemulsion has been found. The volume of the middle phase is determined. The volume of surfactant added is subtracted from this volume. The value obtained is then divided by two. This volume is then divided by the volume of surfactant added. The result is noted as SP*.

The type of oil and water used to determine SP* is determined according to the system to be examined. It is possible either to use mineral oil itself or a model oil, for example decane. The water used may either be pure water or saline water, in order better to model the conditions in the mineral oil formation. The composition of the aqueous phase can be adjusted, for example, according to the composition of a particular deposit water.

Information regarding the aqueous phase used and the oil phase can be found below in the specific description of the tests.

Test Results

A 1:1 mixture of decane and of an NaCl solution was admixed with butyl diethylene glycol (BDG). Butyl diethylene glycol (BDG) functions as a co-solvent and is not included in the calculation of SP*. To this was added a surfactant mixture composed of 3 parts alkyl alkoxysulfate and 1 part dodecylbenzene sulfonate (Lutensit A-LBN 50 ex BASF). The total surfactant concentration is reported in percent by weight of the total volume.

In addition a 1:1 mixture out of decane and sodium chloride solution was mixed with butyl diethylene glycol (BDG). Butyl diethylene glycol (BDG) works as cosolvent and was not taken into account for SP*. Surfactant mixture consisting out of three parts alkyl alkoxy sulfate and one part secondary alkyl sulphonate (Hostapur SAS 60 ex Clariant) was added. Total surfactant concentration in weight percent refers to aqueous phase.

In addition, a 1:1 mixture of south German crude oil (API 33°) and of an NaCl solution was admixed with butyl diethylene glycol (BDG). Butyl diethylene glycol (BDG) functions as a co-solvent and is not included in the calculation of SP*. To this was added a surfactant mixture composed of 3 parts alkyl alkoxy sulfate and 1 part dodecylbenzenesulfonate (Lutensit A-LBN 50 ex BASF). The total surfactant concentration is reported in percent by weight of the total volume.

In two further tests a 1:1 mixture out of crude oil from southern parts of Germany (API) 33° and sodium chloride solution or a 1:1 mixture out or crude oil Canada (API 14°) and sodium chloride solution was mixed each with butyl diethylene glycol (BDG). Butyl diethylene glycol (BDG) works as cosolvent and was not taken into account for SP*. Surfactant mixture consisting out of three parts alkyl alkoxy sulfate and one part secondary alkyl sulphonate (Hostapur SAS 60 ex Clariant) was added each. Each total surfactant concentration in weight percent refers to aqueous phase.

The results for surfactants based on linear and branched alcohols are shown in tables 1 to 7.

As evident from examples C1 and C3 or C2 and C4 in table 1, there are few differences in SP* between $C_{16}C_{18}$-7 PO-sulfate and $C_{16}C_{18}$-9 PO-sulfate. In this respect, it should be noted that a comparison should be carried out at similar $T_{opt}$ in order to rule out temperature effects. These may have a considerable influence in the case of surfactants with nonionic elements.

When BuO-containing $C_{16}C_{18}$-alkoxy sulfates are used, there are surprising findings. Examples 5 and 6 show that the incorporation of two 1,2-butylene oxide units between the $C_{16}C_{18}$-fatty alcohol and the seven propylene oxide units leads to a surprisingly stable SP*=16, no matter whether at 47° C. or at 62° C. A similar picture emerges at reduced total surfactant concentration. In example 11 the SP* is 15 at 72° C. Purely PO-containing compounds with the same degree of alkoxylation show greater variations (C3 and C4), or the SP* declines to a somewhat greater degree at a reduced total surfactant concentration (C9 and C10).

Arrangement of 1,2-butylene oxide between the propylene oxide block and the sulfate group as in comparative examples C7 and C8 is, in contrast, less favorable. SP* is at a somewhat lower level and varies more significantly on consideration of different temperatures.

The use of 2,3-butylene oxide is significantly poorer. As can be seen in C12, SP* is virtually halved at SP*=8, and hence is poorer than alkyl propoxy sulfates with the same degree of alkoxylation (C9). Surprisingly, not the mere number of carbon atoms but also the spatial arrangement thereof has a great influence on the ability of the surfactants to lower the interfacial tension. An unfavorable arrangement as in the case of 2,3-butylene oxide actually has a disruptive effect and gives poorer values than in the case of corresponding surfactants without alkylene oxide having 4 carbon atoms. U.S. Pat. No. 3,890,239 or U.S. Pat. No. 4,448,697 does not describe this.

Interestingly, there is an abrupt improvement as soon as the content of 1,2-butylene oxide units is three or greater in the linear $C_{16}C_{18}$-fatty alcohol. In example 13, the incorporation of three such units leads to a rise in the SP* to 23.5. This can even be enhanced further by going up to 5 units (examples 14-16). SP* is even above 30 here.

TABLE 1

Surfactants based on linear $C_{16}C_{18}$-alcohol

| Ex. | Alkyl-AO-$SO_4$Na:$C_{12}H_{25}$Ph-$SO_3$Na = 3:1 | Surfactant [%] | BDG [%] | NaCl [%] | $T_{opt}$ [° C.] | SP* | IFT [mN/m] |
|---|---|---|---|---|---|---|---|
| C1 | $C_{16}C_{18}$—7PO—$SO_4$Na | 2.5 | 2 | 5 | 48 | 13.3 | 0.0017 |
| C2 | $C_{16}C_{18}$—7PO—$SO_4$Na | 2.5 | 2 | 4 | 60 | 17.8 | 0.0009 |
| C3 | $C_{16}C_{18}$—9PO—$SO_4$Na | 2.5 | 2 | 5 | 52 | 15.5 | 0.0012 |
| C4 | $C_{16}C_{18}$—9PO—$SO_4$Na | 2.5 | 2 | 4 | 67 | 17.8 | 0.0009 |
| 5 | $C_{16}C_{18}$-2 "1,2-BuO"-7PO—$SO_4$Na | 2.5 | 2 | 5 | 47 | 16 | 0.0012 |
| 6 | $C_{16}C_{18}$-2 "1,2-BuO"-7PO—$SO_4$Na | 2.5 | 2 | 4 | 65 | 16.5 | 0.0011 |
| C7 | $C_{16}C_{18}$—7PO-2 "1,2-BuO"-$SO_4$Na | 2.5 | 2 | 4 | 46 | 11.8 | 0.0022 |
| C8 | $C_{16}C_{18}$—7PO-2 "1,2-BuO"-$SO_4$Na | 2.5 | 2 | 3 | 68 | 14.3 | 0.0015 |
| C9 | $C_{16}C_{18}$—9PO—$SO_4$Na | 1.25 | 2 | 5 | 52 | 14 | 0.0015 |
| C10 | $C_{16}C_{18}$—9PO—$SO_4$Na | 1.25 | 2 | 4 | 67 | 13 | 0.0018 |
| 11 | $C_{16}C_{18}$-2 "1,2-BuO"-7PO—$SO_4$Na | 1.25 | 2 | 3.35 | 72 | 15 | 0.0013 |
| C12 | $C_{16}C_{18}$-2 "2,3-BuO"-7PO—$SO_4$Na | 1.25 | 2 | 4.5 | 74 | 8 | 0.0047 |
| 13 | $C_{16}C_{18}$-3 "1,2-BuO"-7PO—$SO_4$Na | 1.25 | 2 | 3 | 67 | 23.5 | 0.0005 |
| 14 | $C_{16}C_{18}$-5 "1,2-BuO"-7PO—$SO_4$Na | 1.25 | 2 | 2 | 77 | 34.5 | 0.0003 |
| 15 | $C_{16}C_{18}$-5 "1,2-BuO"-7PO—$SO_4$Na | 1.25 | 2 | 2.15 | 71 | 35.5 | 0.0002 |
| 16 | $C_{16}C_{18}$-5 "1,2-BuO"-7PO—$SO_4$Na | 1.25 | 2 | 2.5 | 49 | 30.5 | 0.0003 |

TABLE 2

Surfactants based on branched $iC_{17}$-alcohol

| Ex. | Alkyl-AO-SO$_4$Na:C$_{12}$H$_{25}$Ph-SO$_3$Na = 3:1 | Surfactant [%] | BDG [%] | NaCl [%] | T$_{opt}$ [° C.] | SP* | IFT [mN/m] |
|---|---|---|---|---|---|---|---|
| C1 | iC$_{17}$—7PO—SO$_4$Na | 1.25 | 2 | 4 | 77.5 | 10.5 | 0.0027 |
| 2 | iC$_{17}$-7 "1,2-BuO"-SO$_4$Na | 1.25 | 2 | 1 | 82.5 | 32.5 | 0.0003 |
| C3 | iC$_{17}$—14PO—SO$_4$Na | 1.25 | 2 | 4.4 | 77 | 6.5 | 0.0071 |
| 4 | iC$_{17}$—7PO-7 "1,2-BuO"-SO$_4$Na | 1.25 | 2 | 1.65 | 74.5 | 17 | 0.0010 |
| 5 | iC$_{17}$-7 "1,2-BuO"-7PO—SO$_4$Na | 1.25 | 2 | 2.5 | 67.5 | 31.5 | 0.0003 |
| 6 | iC$_{17}$-7 "1,2-BuO"-7PO—SO$_4$Na | 1.25 | 2 | 3 | 50 | 29.5 | 0.0003 |

A similar picture emerges in table 2. Here, alkyl alkoxy sulfates based on the branched $iC_{17}$-alcohol were used to demonstrate that there is an effect which is not attributable to linear alcohols alone.

Comparative example C1 and example 2 show very clearly that the use of 1,2-butylene oxide instead of propylene oxide is distinctly advantageous in surfactants with the same degree of alkoxylation. At a similar temperature, the SP* is three times as high. The arrangement of the 1,2-BuO directly on the alkyl moiety (as in examples 5 and 6) also gives lower interfacial tensions than a different arrangement as, for example, in example 4.

1,2-butylene oxide units than when the surfactant is based on a linear alcohol with similar chain length. However, incorporation of a further amount of 1,2-butylene oxide in the case of the linear alcohol can, as can be seen in example 5, achieve an approximately identical SP* level to that in example 4.

It can be seen in example 6 that the incorporation of 10 EO between sulfate group and PO block can virtually compensate for the additional hydrophobicity of the 7-BuO block; it is thus possible to make a comparison with com-

TABLE 3

Surfactants based on branched $C_{16}$ Guerbet alcohol compared to $C_{16}C_{18}$-alcohol-based surfactants

| Ex. | Alkyl-AO-SO$_4$Na:C$_{12}$H$_{25}$Ph-SO$_3$Na = 3:1 | Surfactant [%] | BDG [%] | NaCl [%] | T$_{opt}$ [° C.] | SP* | IFT [mN/m] |
|---|---|---|---|---|---|---|---|
| C1 | C$_{16}$C$_{18}$—9PO—SO$_4$Na | 1.25 | 2 | 4 | 67 | 13 | 0.0018 |
| 2 | C$_{16}$C$_{18}$-2 "1,2-BuO"-7PO—SO$_4$Na | 1.25 | 2 | 3.35 | 72 | 15 | 0.0013 |
| 3 | C$_{16}$-Guerbet-2 "1,2-BuO"-7PO—SO$_4$Na | 1.25 | 2 | 2.85 | 68 | 27.5 | 0.0004 |
| 4 | C$_{16}$-Guerbet-2 "1,2-BuO"-7PO—SO$_4$Na | 1.25 | 2 | 3 | 64 | 23.5 | 0.0005 |
| 5 | C$_{16}$C$_{18}$-3 "1,2-BuO"-7PO—SO$_4$Na | 1.25 | 2 | 3 | 67 | 23.5 | 0.0005 |
| 6 | C$_{16}$-Guerbet-7 "1,2-BuO"-7PO-10 EO-SO$_4$Na | 0.40 | 2 | 4.5 | 73 | 31 | 0.0003 |
| C7 | C$_{16}$-Guerbet-7PO—SO$_4$Na | 1.25 | 2 | 5 | 70 | 6 | 0.0083 |
| C8 | C$_{16}$-Guerbet-9PO—SO$_4$Na | 1.25 | 2 | 4 | 71 | 9 | 0.0037 |
| C9 | C$_{16}$-Guerbet-6PO—SO$_4$Na | 1.25 | 2 | 5 | 64 | 5 | 0.0120 |
| C10 | C$_{16}$C$_{18}$—6PO—SO$_4$Na | 1.25 | 2 | 5 | 64 | 10 | 0.0030 |
| 11 | C$_{16}$-Guerbet-1 "1,2-BuO"-7PO—SO$_4$Na | 1.25 | 2 | 3.3 | 73 | 10.25 | 0.0029 |

As can be seen in table 3, a similar picture applies hereto. If a surfactant based on a linear alcohol comprises more than two 1,2-BuO units, there is a distinct jump in the SP* and hence a lowering of the interfacial tension. Example 2 compared to examples 3 and 4 shows the difference between the surfactant based on the linear $C_{16}C_{18}$-alcohol and the surfactant based on the branched $C_{16}$ Guerbet alcohol. In the Guerbet-based surfactant, a significantly better SP* is already attained on incorporation of 2 parative example C1 under similar conditions (similar salt content, similar temperature T$_{opt}$).

Without the incorporation of 1,2-butylene oxide, as can be see in comparative examples C7 and C8, the surfactant is merely an average surfactant. Example 11 shows that the incorporation of 1 eq of 1,2-BuO only gives a certain improvement in SP*. Only incorporation of 2 eq of 1,2-BuO gives a significant improvement in the case of the $C_{16}$ Guerbet-based surfactant (example 3).

TABLE 4

Tests with south German crude oil

| Ex. | Alkyl-AO-SO$_4$Na:C$_{12}$H$_{25}$Ph-SO$_3$Na = 3:1 | Surfactant [%] | BDG [%] | NaCl [%] | T$_{opt}$ [° C.] | SP* | IFT [mN/m] |
|---|---|---|---|---|---|---|---|
| C1 | C$_{16}$C$_{18}$—9PO—SO$_4$Na | 0.8 | 2 | 5 | 34.5 | 9.7 | 0.0032 |
| 2 | C$_{16}$C$_{18}$-3 "1,2-BuO"-7PO—SO$_4$Na | 0.8 | 2 | 3.5 | 31 | 15.9 | 0.0012 |
| C3 | C$_{16}$-Guerbet-9PO—SO$_4$Na | 0.8 | 2 | 5.1 | 34 | 5.8 | 0.0089 |
| 4 | C$_{16}$-Guerbet-2 "1,2-BuO"-7PO—SO$_4$Na | 0.8 | 2 | 3.5 | 34 | 15 | 0.0013 |

As can be seen in table 4, a virtually identical picture also emerges with crude oil compared to the tests with decane model oil. Comparative example C1 gives significantly lower SP* values and hence higher interfacial tensions than the BuO-containing surfactant in example 2 at comparable temperature. Comparative example C3 and example 4 show the advantage of the 1,2-butylene oxide in a similar manner.

TABLE 5

Tests will decane at similar temperature and salinity

| Ex. | Alkyl-AO-SO₄Na:Hostapur SAS 60 = 3:1 | Surfactant [%] | BDG [%] | NaCl [%] | $T_{opt}$ [° C.] | SP* | IFT [mN/m] |
|---|---|---|---|---|---|---|---|
| V1 | $C_{16}C_{18}$—7PO-0.1 EO-SO₄Na | 0.4 | 2 | 4.7 | 59.9 | 18.3 | 0.0009 |
| 2 | $C_{16}C_{18}$-7 "1,2-BuO"-7PO-10 EO-SO₄Na | 0.4 | 2 | 4.7 | 64.8 | 37 | 0.0002 |

Aqueous surfactant solution mixed with BDG are clearly soluble under optimum conditions (salinity und $T_{opt}$ and give by addition of oil a 3-phase-system (Winsor Typ III). As shown in table 5 optimum conditions (salinity und $T_{opt}$) are very close by. Right fine tuning of alkoxylation degree as shown in example 2 lead to surfactant, which has a similar hydrophilic-hydrophobic-balance as the surfactant in example V1. SP* in example 2 is much higher. Consequently interfacial tension is much lower.

TABLE 6

Tests with crude oil from Germany (API 33°) at similar temperature and salinity

| Ex. | Alkyl-AO-SO₄Na:Hostapur SAS 60 = 3:1 | Surfactant [%] | BDG [%] | NaCl [%] | $T_{opt}$ [° C.] | SP* | IFT [mN/m] |
|---|---|---|---|---|---|---|---|
| V1 | $C_{16}C_{18}$—7PO-0.1 EO-SO₄Na | 0.4 | 2 | 3.5 | 73 | 24.5 | 0.0005 |
| 2 | $C_{16}C_{18}$-7 "1,2-BuO"-7PO-10 EO-SO₄Na | 0.4 | 2 | 3.5 | 78.5 | 37 | 0.0002 |

Aqueous surfactant solution mixed with BDG are clearly soluble under optimum conditions (salinity und $T_{opt}$ and give by addition of oil a 3-phase-system (Winsor Typ III). As shown in table 6 optimum conditions (salinity und $T_{opt}$) are very close by. Right fine tuning of alkoxylation degree as shown in example 2 lead to surfactant, which has a similar hydrophilic-hydrophobic-balance as the surfactant in example V1. SP* in example 2 is again much higher. Consequently interfacial tension is much lower.

TABLE 7

Tests with crude oil from Canada (API 14) at similar temperature and salinity

| Ex. | Alkyl-AO-SO₄Na:Hostapur SAS 60 = 3:1 | Surfactant [%] | BDG [%] | NaCl [%] | $T_{opt}$ [° C.] | SP* | IFT [mN/m] |
|---|---|---|---|---|---|---|---|
| V1 | $C_{16}C_{18}$—7PO-0.1 EO-SO₄Na | 0.4 | 2 | 7 | 55 | 12 | 0.0021 |
| 2 | $C_{16}C_{18}$-7 "1,2-BuO"-7PO-10 EO-SO₄Na:$C_{16}C_{18}$-7 "1,2-BuO"-7PO-8 EO-SO₄Na = 2 | 0.4 | 2 | 7 | 57 | 19.5 | 0.0008 |

Aqueous surfactant solution mixed with BDG are clearly soluble under optimum conditions (salinity und $T_{opt}$ and give by addition of oil a 3-phase-system (Winsor Typ III). As shown in table 7 optimum conditions (salinity und $T_{opt}$) are very close by. Right fine tuning of alkoxylation degree as shown in example 2 lead to surfactant, which has a similar hydrophilic-hydrophobic-balance as the surfactant in example V1. SP* in example 2 is again much higher. Consequently interfacial tension is much lower.

The invention claimed is:

1. An aqueous surfactant formulation comprising at least one ionic surfactant of the general formula

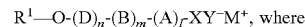

$R^1$—O-(D)$_n$-(B)$_m$-(A)$_l$XY⁻M⁺, where $R^1$ is selected from: iso-$C_{17}H_{35}$; a fatty alcohol mixture with linear $C_{16}H_{33}$ and $C_{18}H_{37}$ alkyl chains; derived from a $C_{16}$ Guerbet alcohol, 2-hexyldecan-1-ol; derived from a $C_{24}$ Guerbet alcohol, 2-decyltetradecanol; or derived from a $C_{28}$ Guerbet alcohol, 2-dodecylhexadecanol, A is ethyleneoxy, B is propyleneoxy, and D is butyleneoxy, l is from 0 to 99, m is from 5 to 9, and n is from 2 to 10, X is an alkyl or alkylene group having 0 to 10 carbon atoms, M⁺ is a cation, and Y⁻ is selected from the group consisting of sulfate groups, sulfonate groups, carboxylate groups and phosphate groups, where the A, B and D groups are in the form of two, three, four or more blocks beginning at the alcohol with the sequence D-B-A, the sum of l+m+n is in the range from 7 to 99 and the proportion of 1,2-butylene oxide, based on the total amount of butylene oxide, is at least 80%.

2. The surfactant formulation according to claim 1, wherein

Y⁻ is selected from the group of sulfate groups, sulfonate groups, and carboxylate groups, where the A, B and D groups are present to an extent of more than 80% in block form, the sum of l+m+n is in the range from 7 to 49, and the proportion of 1,2-butylene oxide, based on the total amount of butylene oxide in the molecule, is at least 90%.

3. The surfactant formulation according to claim 2, wherein $R^1$ is a linear fatty alcohol having 16 or 18 carbon atoms and n is from 3 to 10.

4. The surfactant formulation according to claim 1, wherein the concentration of all surfactants together is 0.05 to 5% by weight, based on the total amount of the aqueous surfactant formulation.

5. A surfactant of the general formula $R^1$—O-(D)$_n$-(B)$_m$-(A)$_l$-XY⁻M⁺, where $R^1$ is selected from: iso-$C_{17}H_{35}$; a fatty alcohol mixture with linear $C_{16}H_{33}$ and $C_{18}H_{37}$ alkyl chains; derived from a $C_{16}$ Guerbet alcohol, 2-hexyldecan-1-ol; derived from a $C_{24}$ Guerbet alcohol, 2-decyltetradecanol; or derived from a $C_{28}$ Guerbet alcohol, 2-dodecylhexadecanol, A is ethyleneoxy,
B is propyleneoxy, and
D is butyleneoxy,
l is from 0 to 99,
m is from 5 to 9 and
n is from 2 to 10,
X is an alkyl or alkylene group having 0 to 10 carbon atoms,
M⁺ is a cation, and Y⁻ is selected from the group consisting of sulfate groups, sulfonate groups, carboxylate groups and phosphate groups, where the A, B and D groups are in the form of two, three, four or more blocks beginning at the alcohol with the sequence D-B-A, the sum of l+m+n is in the range from 7 to 99 and the proportion of 1,2-butylene oxide, based on the total amount of butylene oxide, is at least 80%.

6. The surfactant according to claim 5, wherein the sum of l+m+n is in the range from 7 to 49.

7. The surfactant according to claim 5, Wherein the proportion of 1,2-butylene oxide, based on the total amount of butylene oxide, is at least 90%.

8. The surfactant according to claim 5, wherein $R^1$ is a fatty alcohol mixture with linear $C_{16}H_{33}$ and $C_{18}H_{37}$ alkyl chains, n is from 3 to 10, and Y⁻ is selected from the group consisting of sulfate groups, sulfonate groups, and carboxylate groups, where the A, B and D groups are present to an extent of more than 80% in block form, the sum of l+m+n is in the range from 7 to 49, and the proportion of 1,2-butylene oxide, based on the total amount of butylene oxide in the molecule, is at least 90%.

9. The surfactant according to claim 5, wherein $R^1$ is a linear fatty alcohol having 16 or 18 carbon atoms and n is from 3 to 10.

10. The surfactant according to claim 5, wherein $R^1$ is a linear fatty alcohol having 16 or 18 carbon atoms and the surfactant is selected from the group consisting of $R^1O-D_2-B_7$—XY⁻M⁺, $R^1O-D_3-B_7$—XY⁻M⁺, $R^1O-D_5-B_7$—XY⁻M⁺, and $R^1O-D_7-B_7A_{10}$-XY⁻M⁺.

11. The surfactant according to claim 5, wherein $R^1$ is a $C_{16}$ Guerbet alcohol, 2-hexyldecan-1-ol.

* * * * *